United States Patent [19]

Green et al.

[11] Patent Number: 5,352,238
[45] Date of Patent: * Oct. 4, 1994

[54] APPARATUS FOR APPLYING TWO-PART SURGICAL FASTENERS

[75] Inventors: David T. Green, Westport; Henry Bolanos, East Norwalk; Robert J. Geiste, Milford, all of Conn.; Wayne P. Young, Brewster, N.Y.; Stephen W. Gerry, Bethel; Frank M. Rende, III, Stamford, both of Conn.

[73] Assignee: United States Surgical Corporation, Norwalk, Conn.

[ * ] Notice: The portion of the term of this patent subsequent to Oct. 20, 2009 has been disclaimed.

[21] Appl. No.: 962,279

[22] Filed: Oct. 16, 1992

Related U.S. Application Data

[63] Continuation of Ser. No. 794,596, Nov. 14, 1991, Pat. No. 5,156,614.

[51] Int. Cl.5 .............................................. A61B 17/00
[52] U.S. Cl. .................................... 606/220; 227/176; 227/178; 227/180
[58] Field of Search ........... 606/220; 227/19, 175–188

[56] References Cited

U.S. PATENT DOCUMENTS

| | | |
|---|---|---|
| 3,079,606 | 3/1963 | Bobrov et al. . |
| 3,490,675 | 1/1970 | Green et al. . |
| 3,499,591 | 3/1970 | Green . |
| 3,844,289 | 10/1974 | Noiles . |
| 4,086,926 | 5/1978 | Green et al. . |
| 4,204,623 | 5/1980 | Green . |
| 4,256,251 | 3/1981 | Moshofsky ............................. 227/120 |
| 4,354,628 | 10/1982 | Green . |
| 4,391,401 | 7/1983 | Moshofsky ............................. 227/19 |
| 4,429,695 | 2/1984 | Green . |
| 4,473,077 | 9/1984 | Noiles et al. . |
| 4,506,670 | 3/1985 | Crossley . |
| 4,520,817 | 6/1985 | Green ..................................... 227/19 |
| 4,576,165 | 3/1986 | Green et al. . |
| 4,576,167 | 3/1986 | Noiles . |
| 4,589,416 | 5/1986 | Green . |
| 4,597,517 | 7/1986 | Wagdy . |
| 4,606,345 | 8/1986 | Dorband et al. . |
| 4,608,981 | 9/1986 | Rothfuss et al. ..................... 227/180 |
| 4,633,861 | 1/1987 | Chow et al. ........................... 227/180 |
| 4,633,874 | 1/1987 | Chow et al. ........................... 227/180 |
| 4,664,305 | 5/1987 | Blake, III et al. ..................... 227/19 |
| 4,665,916 | 5/1987 | Green ..................................... 227/178 |
| 4,686,983 | 8/1987 | Leisman et al. . |
| 4,809,898 | 3/1989 | Gassner et al. ........................ 227/8 |
| 4,863,088 | 9/1989 | Redmond et al. . |
| 4,881,544 | 11/1989 | Green et al. . |
| 4,892,244 | 1/1990 | Fox et al. . |
| 4,932,960 | 6/1990 | Green et al. . |
| 4,955,959 | 9/1990 | Tompkins et al. .................... 227/178 |
| 5,031,814 | 7/1991 | Tompkins et al. . |
| 5,083,695 | 1/1992 | Foslien et al. . |
| 5,106,008 | 4/1992 | Tompkins et al. .................... 227/178 |
| 5,129,570 | 7/1992 | Schulze et al. . |
| 5,141,144 | 8/1992 | Foslien et al. . |

Primary Examiner—Stephen C. Pellegrino
Assistant Examiner—Gary Jackson

[57] ABSTRACT

Apparatus for applying at least one row of two-part surgical fasteners to body tissue, each surgical fastener having a pronged fastener portion for piercing body tissue, and an aperture retainer dimensioned and configured for engaged reception of the pronged fastener portion in interference fit therewith for gripping the body tissue therebetween. The apparatus includes means for holding a plurality of the fastener portions in generally aligned relation, means spaced from the fastener portion holding means for gripping body tissue therebetween and for releasably holding a plurality of the retainers in generally aligned relation and positioned opposite the fasteners when the body tissue is positioned therebetween. Means is provided for sequentially advancing the pronged fastener portions toward the apertured retainers to cause the fastener portions to pierce the body tissue and to be received within the apertures of the retainers in engaged interference relation so as to cause the fastener portions and the retainers to be engaged while gripping the body tissue therebetween. In the preferred embodiment a knife edge is provided to cut the body tissue midway between opposed pairs of rows of the fasteners as the fasteners are applied. A method for applying two spaced apart pairs of rows of the fasteners to body tissue on the apparatus of the invention is also disclosed.

16 Claims, 14 Drawing Sheets

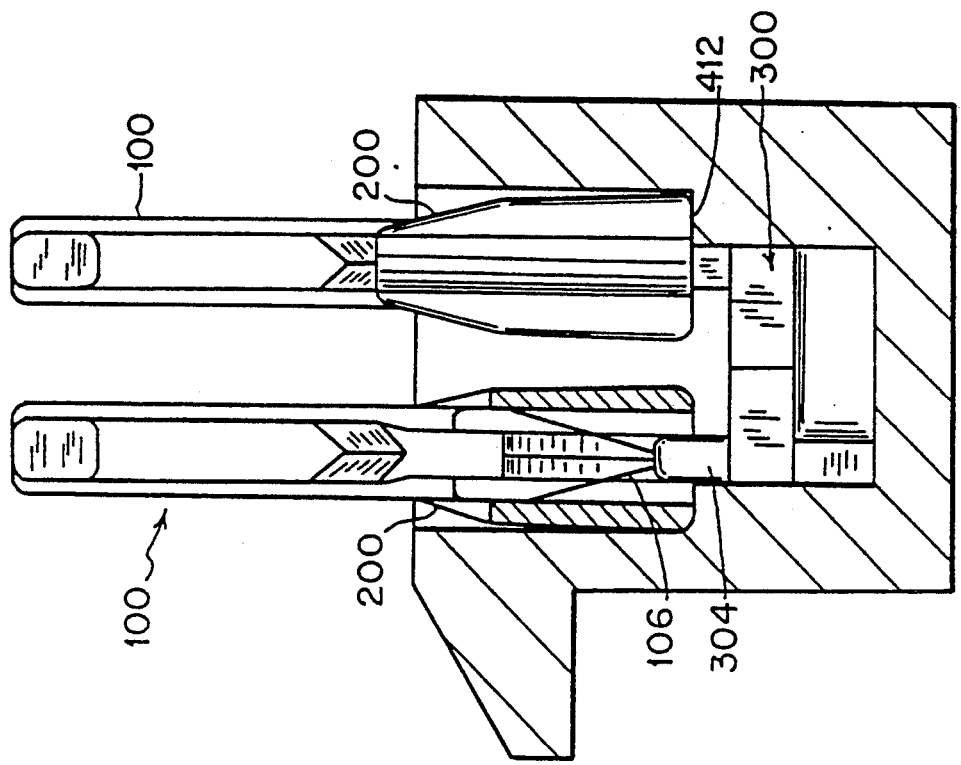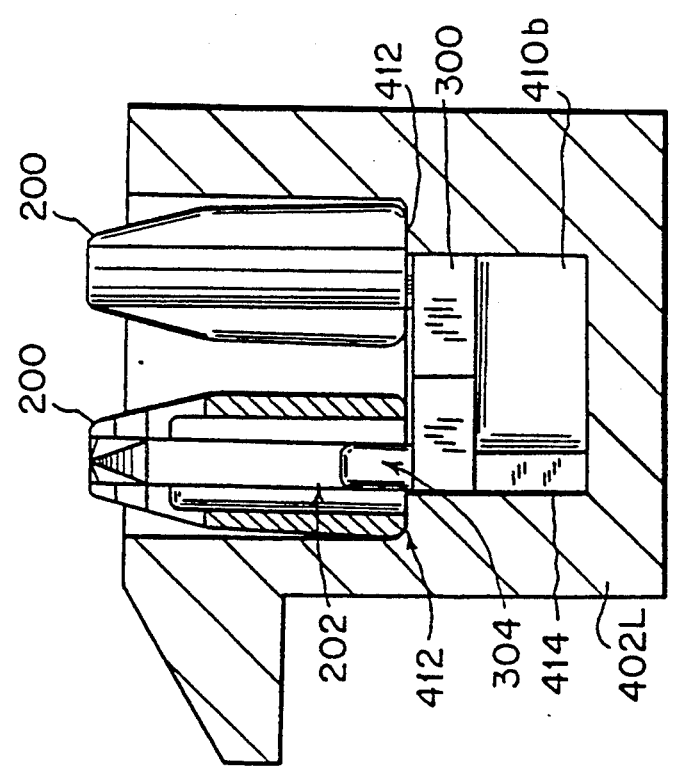

APPARATUS FOR APPLYING TWO-PART SURGICAL FASTENERS

This is a continuation of copending application Ser. No. 07/794,596, filed Nov. 14, 1991.

BACKGROUND OF THE INVENTION

1. Field of the Invention

This invention relates to an apparatus for applying surgical fasteners and more particularly, to a fastener applying apparatus having an improved fastener cartridge and holder for the retainer portion of two-part surgical fasteners.

2. Background of the Prior Art

In some surgical operations it is necessary to adjoin two hollow body organs alongside each other, with their longitudinal axes positioned generally parallel to each other, and to effect a longitudinal cut through the contacting circumferential walls of the two organs in order to open them to each other. After joining the two organs they essentially constitute a single hollow chamber along the length of the cut. Correspondingly, the circumferential portions of the two adjoining organs on each lateral side of the cut must be sutured by at least one line of "stitches" in order to maintain the integrity of the union.

Instruments for this purpose are known in the art, and are described in U.S. Pat. Nos. 3,079,606, 3,490,675 and 3,499,591. Such instruments are generally referred to as linear cutting staplers and include two elongate fingers which are respectively insertable into each organ from an open end thereof such that the two fingers have the adjoining walls of the adjacent organs therebetween. Further examples of such instruments are disclosed in commonly assigned U.S. Pat. Nos. 4,429,695 and 4,520,817. The disclosures of these two last mentioned patents are incorporated herein by reference.

One of the fingers includes a disposable cartridge carrying a plurality of staples arranged in at least two lateral rows while the other finger includes an anvil for curling the staple legs into hook form upon being driven against the anvil. The stapling operation is effected by a pusher device which travels longitudinally along the cartridge carrying finger extending into one organ. The pusher mechanism acts simultaneously upon the staples at corresponding longitudinal positions in each lateral row, but successively acts upon the staples along the rows. For example, if two laterals rows of staples are provided, each row comprising twenty staples, the pusher means acts upon two staples at a time, one in each row, and successively acts upon each succeeding pair of staples.

Immediately behind the pusher means and laterally positioned between the staple rows is a knife member which severs the facing adjoining walls of the two organs to thereby longitudinally open the two organs to each other between the rows of staples.

Up to the present these devices were limited to applying metal staples. Two-part absorbable fasteners, such as those used in devices described in U.S. Pat. No. 4,665,916, hereby incorporated by reference, have been limited to devices which apply all of the fasteners simultaneously. Indeed, the retainer members of such absorbable fastener devices typically have been constructed as a web of retainers interconnected by flexible or frangible members. See, for example, U.S. Pat. No. 4,589,416. Devices of the type shown in the aforementioned U.S. Pat. Nos. 3,079,606; 3,490,675 and 3,499,591, on the other hand, employ an actuating cam bar which travels substantially perpendicularly to the direction of fastener motion to effect sequential placement of staples.

Up to the present, applying two-part absorbable fasteners with instruments of the type disclosed in U.S. Pat. Nos. 3,079,606; 3,490,675 and 3,499,591 has not been possible due in part to the peculiar difficulties inherent in aligning the separate fasteners and retainers. The present invention relates to an apparatus which successfully combines a system of applying such fasteners sequentially while cutting the tissue and effecting complete closures.

SUMMARY OF THE INVENTION

An apparatus is disclosed for applying at least one row of two-part surgical fasteners, each surgical fastener having a pronged fastener portion and a retainer, which comprises means for holding the fastener portions of the two part surgical fasteners, a retainer cartridge having means for holding a plurality of retainers in positions opposite the fastener portions, a plurality of retainer mounting elements located in the retainer cartridge for releasably engaging and holding the retainers. The fastener portions and retainers are arranged in longitudinal alignment with the axis of the apparatus, and the fastener portions are sequentially driven into engagement with their respective retainers, and means for sequentially driving the fastener portions of the two part fasteners into engagement with the respective opposed retainers.

The retainer mounting elements are slidably mounted within a lower channel in the retainer cartridge and arranged to release their respective retainers in response to the engagement of the fastener portions with their respective retainers. Further, the retainer mounting elements each comprise a base portion and at least one upright post for engaging an aperture in the retainer and frictionally holding the retainer. A surface portion of the upright post is preferably inclined on at least one vertical side and backstop means is provided for bracing the retainers when engaging with the fastener portions. The backstop means comprises a horizontal shelf portion of the cartridge upon which the retainers at least partially rest. The lower and upper channels have vertical side walls, and the lower channel is of lesser width than the upper channel and is located below the upper channel thereby forming at least one shelf portion. The lower channel has a plurality of vertical guide rails and the retainer mounting elements each have at least one vertical notch for cooperating with a respective one of the vertical guide rails. Preferably the two-part surgical fasteners are bio-absorbable and the apparatus is adapted to fasten body tissue therewith.

The preferred embodiment of the apparatus comprises a two part frame having separable sections capable of releasable attachment to each other and each having an elongated finger portion. A fastener carrying cartridge is mounted along one of the finger portions and carries a plurality of the fastener portions, and a retainer carrying cartridge is mounted along the other finger portion opposite the fastener cartridge and carries a plurality of the retainer members positioned opposite the fastener portions. A pair of cam bars is positioned for slidable movement distally and proximally within the frame for sequential engagement with the fastener pushers.

A generally U-shaped shoe plate is provided between each fastener and retainer cartridge and the respective channel members of the frame. Each shoe plate defines a channel for reception of a respective shoe associated with the cam bars. The respective shoes prevent separation of the frame members when the cam bars are advanced a predetermined distance due to the entry of said shoes associated therewith into the channels defined by the shoe plates.

A method is disclosed for applying at least one row of two-part surgical fasteners, each surgical fastener having a pronged fastener portion and a retainer, comprising, holding the fastener portions of the two-part surgical fasteners, releasably holding a plurality of retainers in positions opposite the fastener portions, and sequentially driving the fastener portions of the two-part fasteners into engagement with their respective opposed retainers. Each surgical fastener has a pronged generally U-shaped fastener portion, and an apertured retainer dimensioned for engaged reception of the fastener portion. Preferably the method comprises holding a plurality of the fastener portions, releasably holding a plurality of the retainers in positions opposite the fastener portions such that the apertures thereof face the pronged portions of the fastener portions, and sequentially driving the fastener portions of the two-part fasteners toward the retainers so as to cause the pronged portions to be engagably received within the apertures of the retainers. Preferably two rows of fastener portions and mating retainers are provided.

According to the method, body tissue to be fastened is positioned between the rows of fastener portions and retainers such that sequentially driving the fastener portions toward the retainers causes the fastener portions to be driven through the tissue so as to grip the tissue between the fastener portions and the retainers. The method further comprises cutting the tissue while driving the fastener portions toward the retainers.

The method is preferably accomplished on an apparatus which permits release of the tissue after the fastening and engagement of the two-part fasteners is complete.

BRIEF DESCRIPTION OF THE DRAWINGS

Preferred embodiments of the invention are described hereinbelow with reference to the drawings wherein:

FIG. 16A illustrating in cross-sectional view, further details of the retainer portion of a two-part surgical fastener positioned on a retainer mounting element in the pre-fired position;

FIG. 16B illustrates in cross-sectional view, the retainer portion of a two-part surgical fastener positioned on a mounting element in the fired position.

DETAILED DESCRIPTION OF THE PREFERRED EMBODIMENTS

Figure 1:
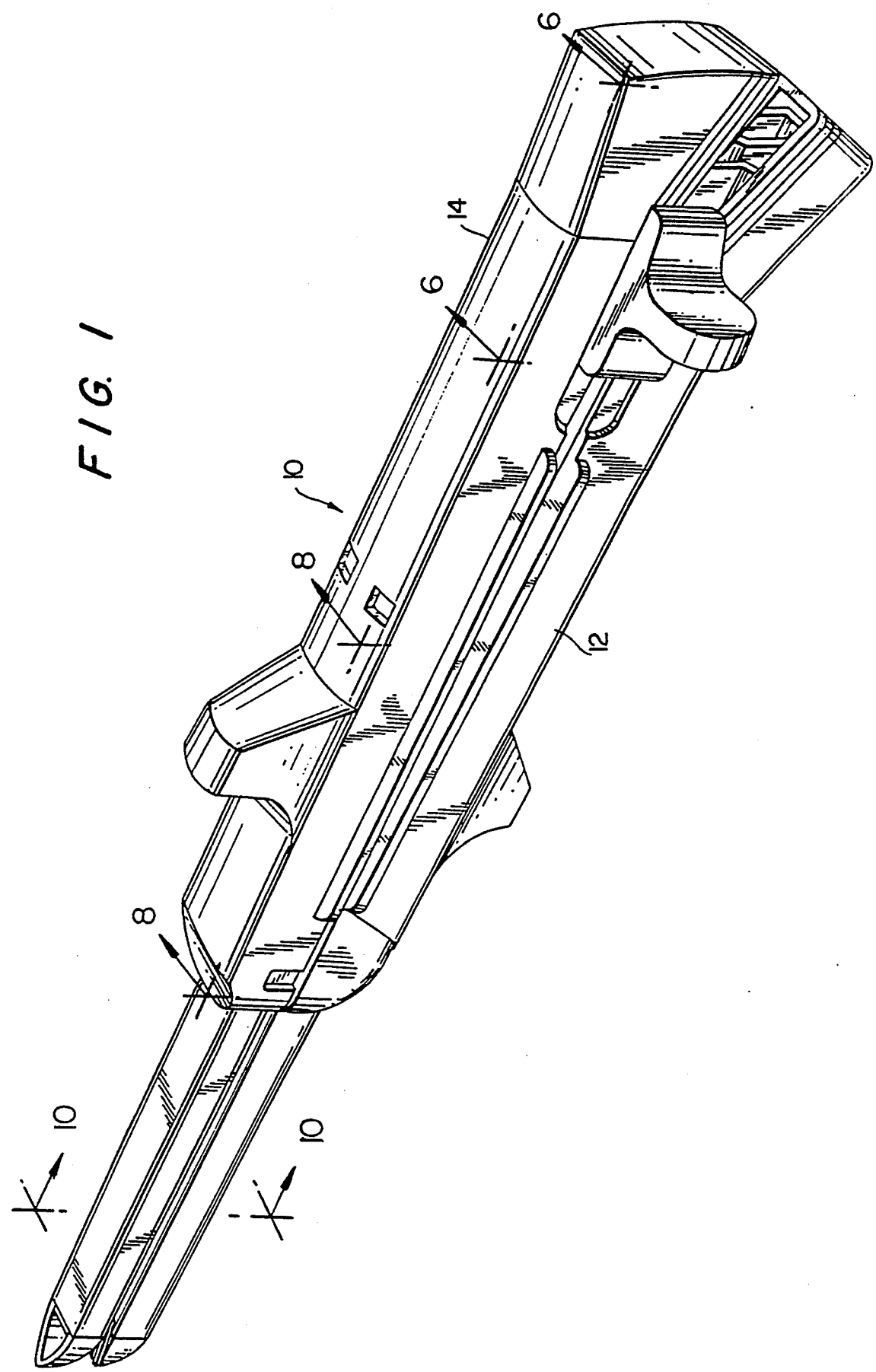
FIG. 1 is a perspective view of the apparatus for applying two-part surgical fasteners constructed according to the present invention.
Figure 2:
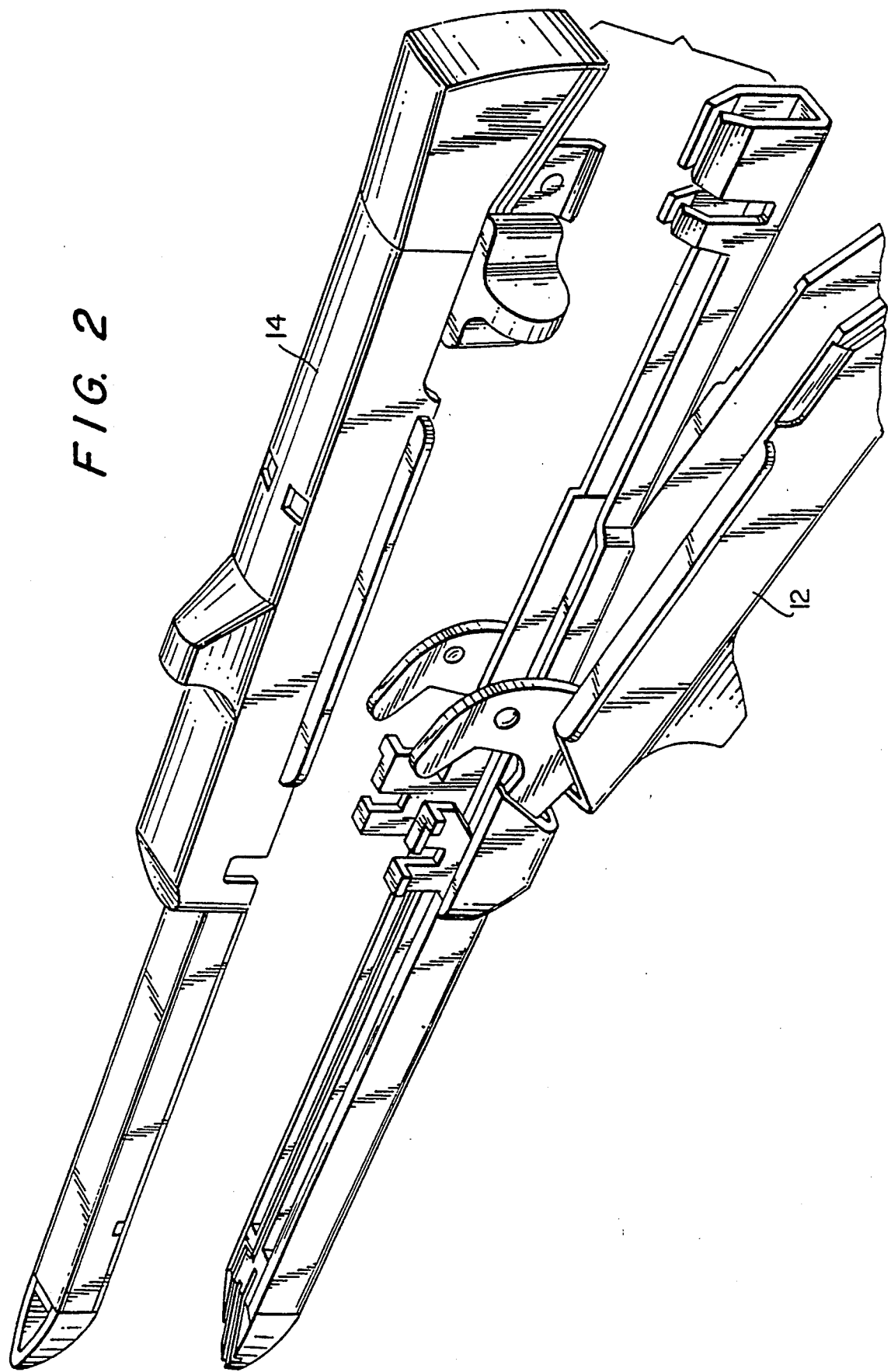
FIG. 2 is an exploded perspective view of the apparatus of FIG. 1, illustrating the two half sections of the fastener applying mechanism.

Referring initially to FIG. 1, there is illustrated a perspective view of the apparatus 10 for applying two-part fasteners constructed according to the present invention. The apparatus 10 includes half sections 12 and 14 as shown, which are adapted to be clamped together in a manner to be described. The two half sections 12 and 14 are shown in perspective view in FIG. 2 and each half section is shown with parts separated in FIGS. 3 and 4.

Figure 3:
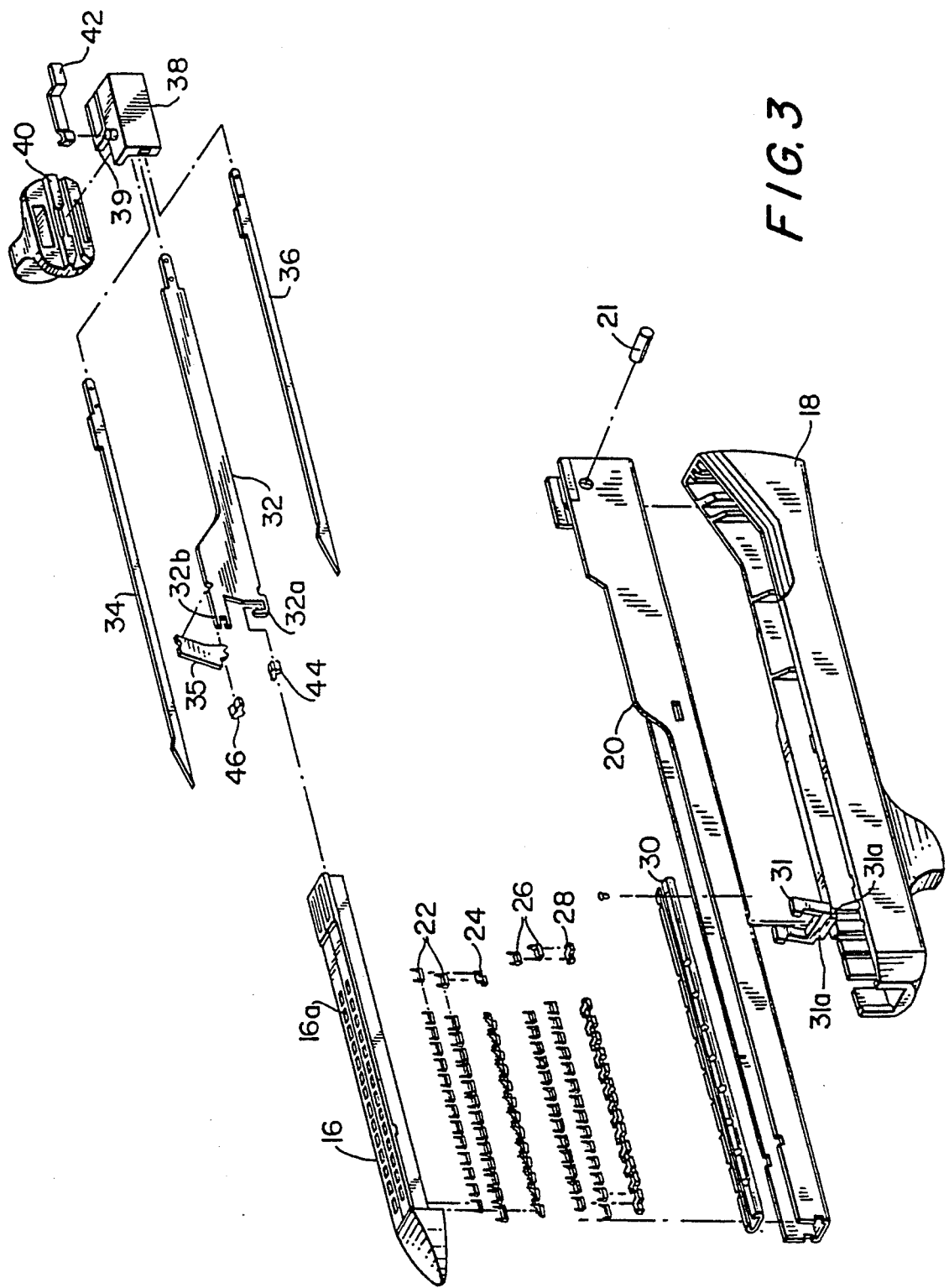
FIG. 3 is an exploded perspective view with parts separated, of the fastener cartridge and associated handle mechanism.

Referring now to FIG. 3, half section 12 for receiving and supporting fastener cartridge 16 is shown. The handle section includes body 18, which receives fastener channel 20. Fastener cartridge 16 receives two staggered rows of U-shaped fasteners. A first pair of rows of fastener portions such as fasteners 22 is disposed on one side of a knife bar 32 and is provided with corresponding fastener pushers 24. A second similar string of a pair of U-shaped fasteners 26 are advanced by corresponding pushers 28 on the other side of knife bar 32. Fasteners 22 and 26 are maintained within suitable spaces 16a provided in cartridge 16 which are dimensioned to frictionally support the fasteners until ejected by the pushers. Shoe plate 30 is provided as shown for slidable reception of a fastener shoe 44.

Referring further to FIG. 3, knife bar 32 is flanked by cam bars 34 and 36 which are connected to bar retainer 38 which in turn is connected to finger pad 40 for finger operated motion of the cam bars 34,36. A retainer spring 42 is provided for engagement with the pivoted handle of the retainer half section (to be described below) to retain the apparatus in the locked condition when the handle is closed. Fastener shoe 44 is attached to knife bar 32 at tab 32a on the fastener side and retainer shoe 46 is attached to knife bar 32 at tab 32b on the retainer side as shown. As will be described in further detail, fastener shoe 44 and retainer shoe 46 slide within respective shoe plates 30,50 (FIGS. 3 and 4) and serve to secure the two half sections 12,14 together after the knife bar is advanced a predetermined amount in order to prevent separation of the half sections. Also, the shoes 44,46 and the shoe plates serve to control the gap between the fastener cartridge and the retainer cartridge and thus the relative positions of the fastener portion and the retainer portion. Knife 35 having a sharp knife edge is attached to knife bar 32 as shown for cutting tissue simultaneously with the fastening operation. Knife 35 lags the cam bars a small distance, i.e. about 5 mm.

Figure 4:
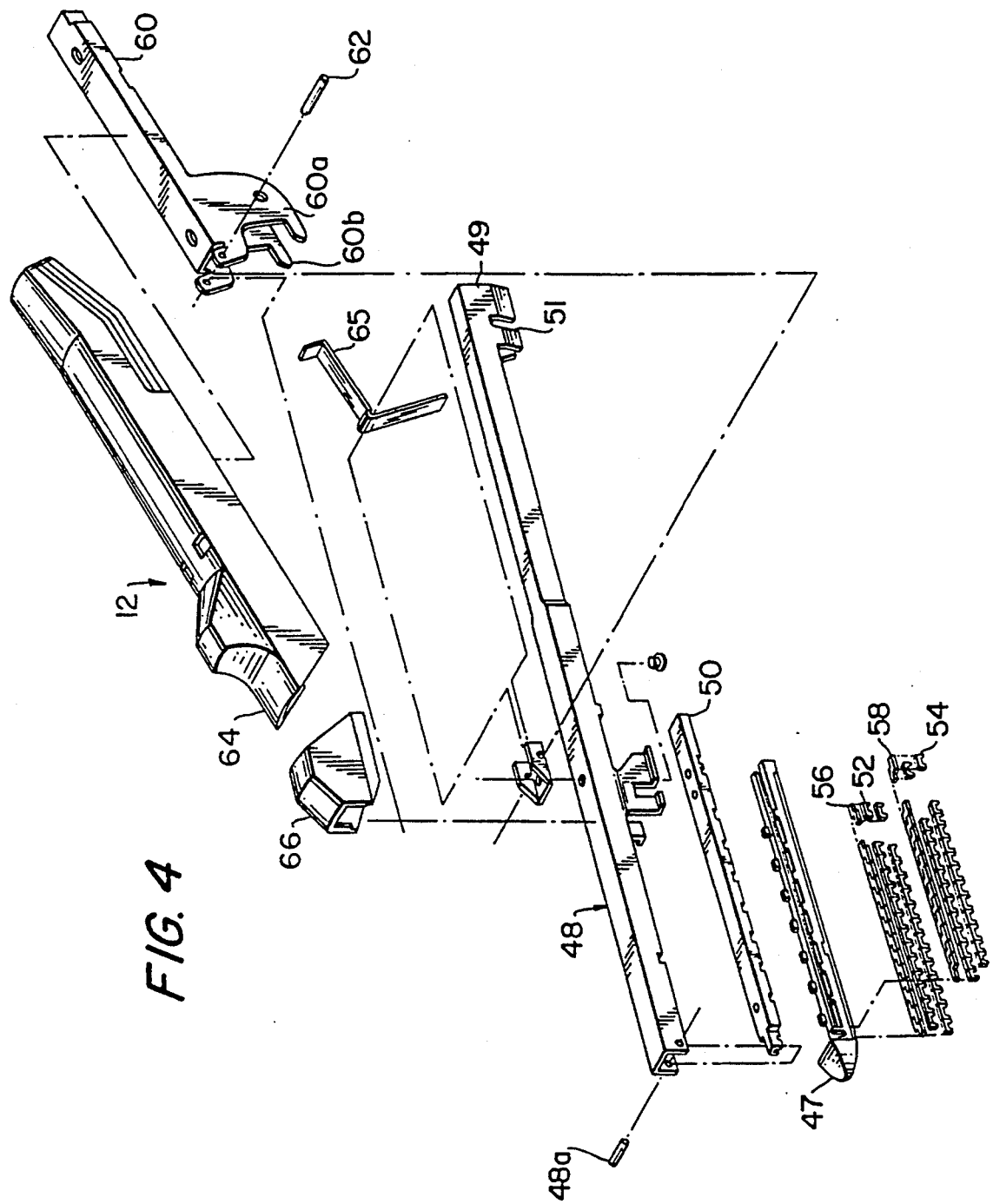
FIG. 4 is an exploded perspective view with parts separated, of the retainer cartridge and associated handle mechanism.

Referring now to FIG. 4 the retainer half section 12 is illustrated with parts separated. Retainer channel 48 is provided with retainer shoe plate 50 and retainer cartridge 47 for supporting two staggered rows of retainers 52 and 54, with associated retainer holders 56 and 58. The retainers are each precisely positioned opposite a respective fastener when the half sections of the apparatus are assembled.

Handle clamp 60 is pivotally attached to channel 48 via pin 62 with leaf spring 65 positioned therebetween to resiliently bias handle clamp 60 away from retainer channel 48. Handle cap 64 is attached to handle clamp 60 and nose cap 66 is provided as shown at the distal end of cap 64.

Figure 5:
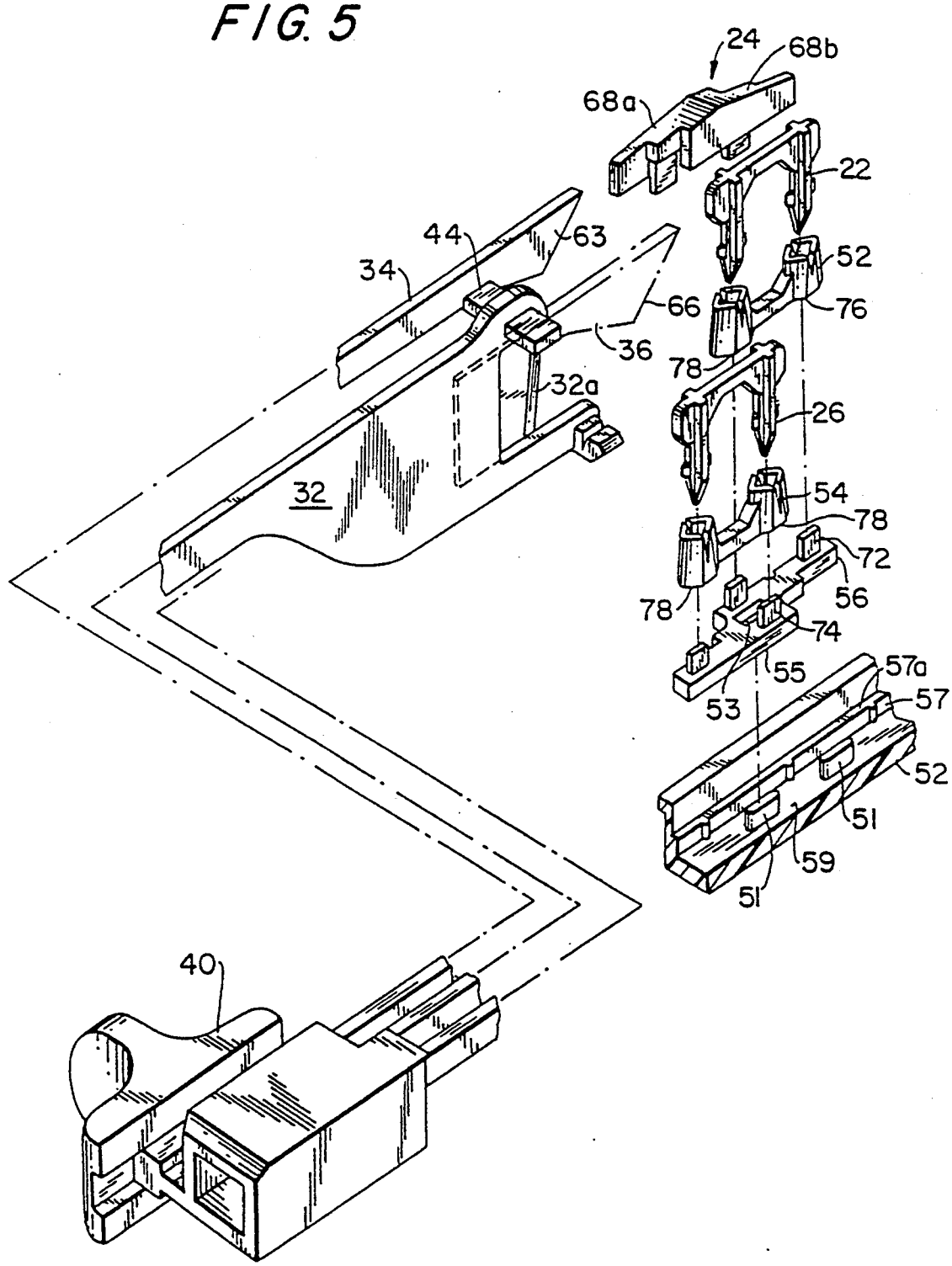
FIG. 5 is an exploded perspective view of the operable portions of the apparatus of FIG. 1, illustrating the mechanism for advancing camming fingers and a tissue cutting blade to secure the two part fastener/retainer and for cutting adjacent tissue.
Figure 10:
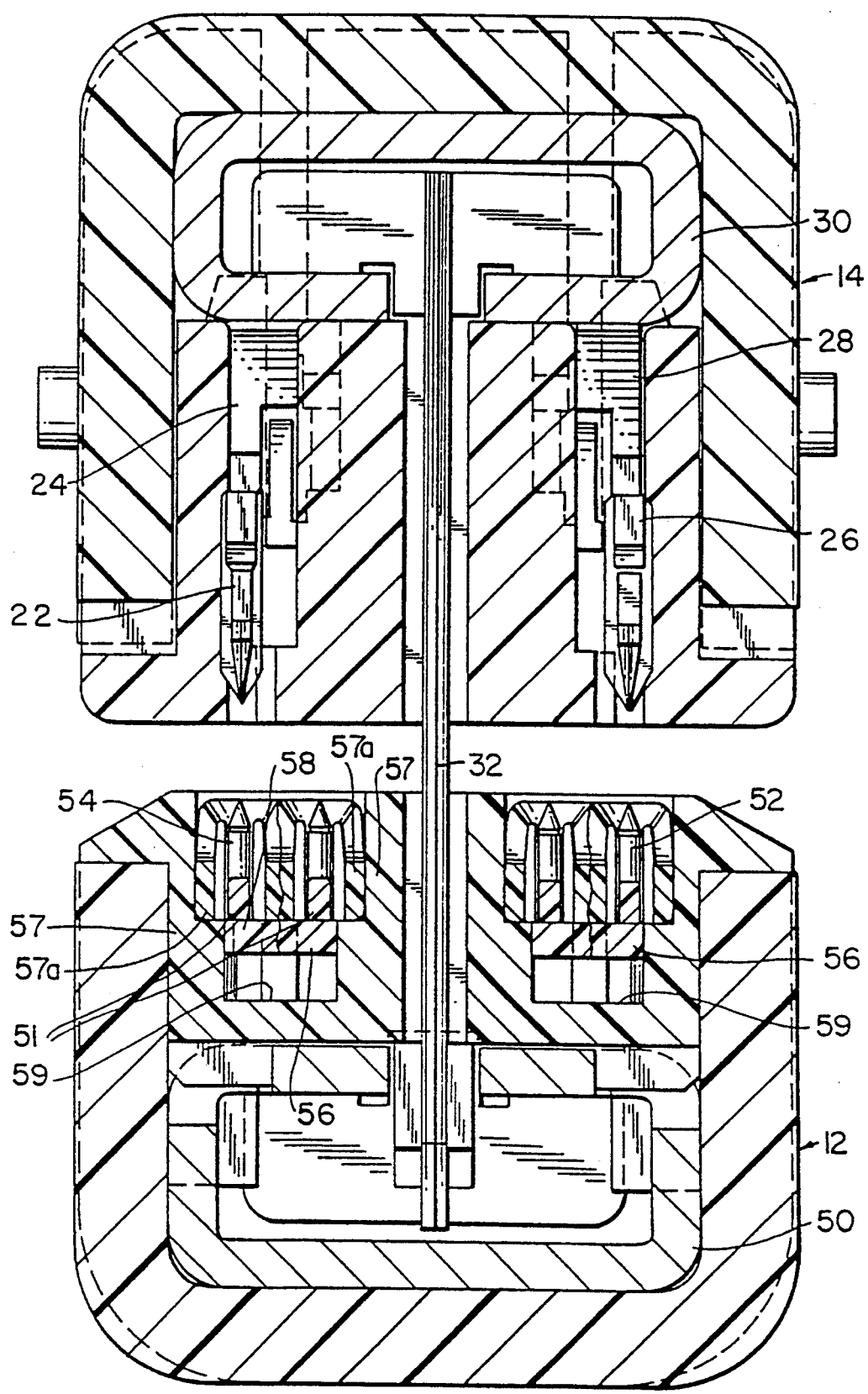
FIG. 10 is a cross-sectional view taken along lines 10—10 of FIG. 1, illustrating the relative positions of the fasteners and retainers prior to firing the apparatus.

Referring now to FIG. 5, the motion of knife bar 32 and associated cam bars 34,36 is illustrated. When finger pad 40 is moved distally by the surgeon, the distal sloped surfaces 64,66 of cam bars 34,36 engage the corresponding proximal surfaces 68a and 70a (not shown in FIG. 5) of fastener pushers 24 and 28 (not shown in FIG. 5), causing movement of the pushers in a direction substantially perpendicular to movement of cam bars 34, 36 and engagement with fasteners 22 and 26. This movement causes the fasteners to move transversely toward corresponding retainers which are at this time, secured in upstanding relation to retainer monitoring elements shown as retainer holders 56 and 58 (holder 58 not shown in FIG. 5) by insertion of upstanding posts 72,74 into the apertures 76,78 on the side of retainers 52,54 opposite the fastener side. Similarly, the retainer holders 56,58, prior to firing the fasteners, are positioned within cartridge 47 such that the top surfaces of the posts 72,74 are approximately at the level of the surfaces 57a of the side rails 57 of retainer cartridge 47 as shown in FIGS. 5 and 10. The retainer holders 56,58 are dimensioned to be positioned between rails 57 of the cartridge 52 with slight frictional fit to maintain the position shown in FIG. 10. This position permits the movement of holder 55 toward the lower surface 59 of cartridge 52 during firing such that posts 51 enter central apertures 53 of the holders 56 to assist in continued alignment of the fastener retainers 26 with the fasteners 27. Additional details relating to the fasteners and retainers will be provided in conjunction with FIGS. 12-17.

Figure 6:
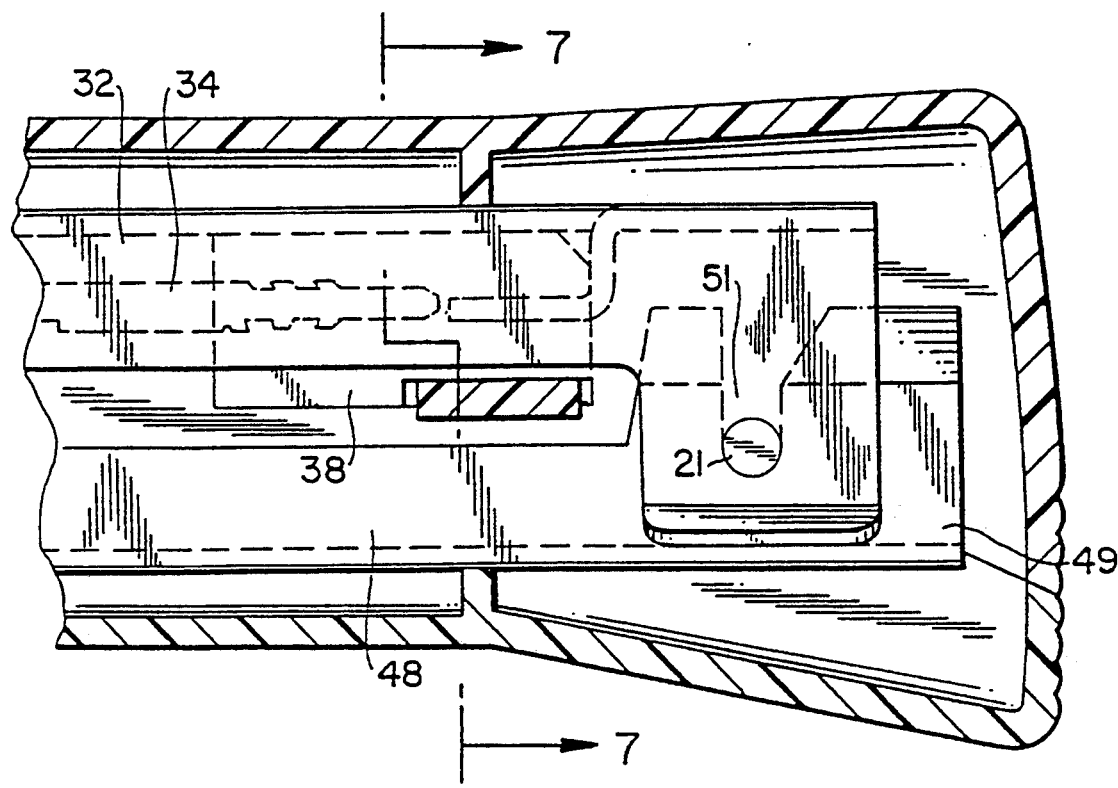
FIG. 6 is a view, partially in cross-section, taken along lines 6—6 of FIG. 1 illustrating the finger operated pad and related mechanism for advancement of the tissue cutting knife and fastener closure cam bars.
Figure 7:
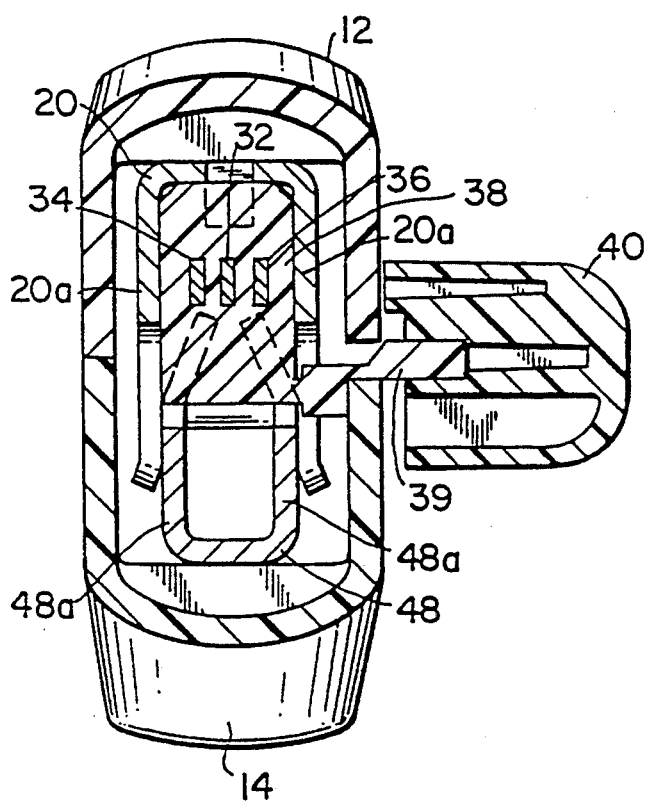
FIG. 7 is a cross-sectional view taken along lines 7—7 of FIG. 1 illustrating the finger operated advancement mechanism for cutting tissue and effecting closure.

Referring now to FIGS. 6 and 7 the finger operated pad and associated mechanism for advancing the tissue cutting knife and fastener closure cam bars are shown. FIG. 6 is a cross-sectional view taken along lines 6—6 of FIG. 1, and FIG. 7 is a cross-sectional view taken along lines 7—7 of FIG. 6. Pad 40 is connected to bar retainer 38 by stem 39 with cam bars 34,36 and knife bar 32 connected at their proximal end portions to bar retainer 38 (see also FIG. 3). The proximal end portion 49 of retainer channel 48 has a cut-out portion 51 (FIGS. 4 and 6). A pin 21 is inserted in fastener channel 20 and positioned within cut-out portion 51 to facilitate alignment of the retainer channel 48 with fastener channel 20 as shown in FIG. 6. Further alignment of the half sections 12, 14 of the apparatus is provided by the side walls 20a, 48a of the channels 20,48, respectively, as shown in FIG. 7, wherein the side walls 48a of channel 48 are slidably and snugly positioned within sidewalls 20a of channel 20 when the half sections 12, 14 of the apparatus are assembled.

Figure 8:
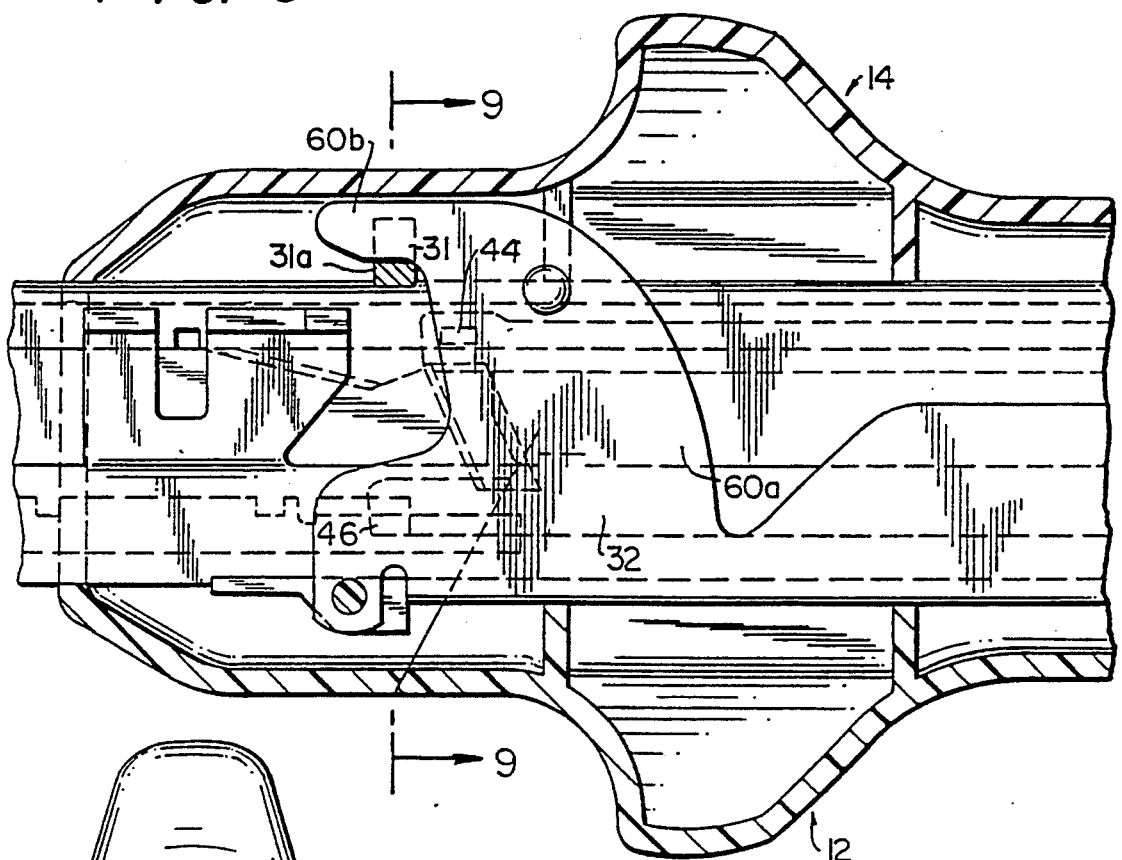
FIG. 8 is a view, partially in cross-section, taken along lines 8—8 of FIG. 1, illustrating the attachment mechanism for securing the two half sections of the apparatus together.
Figure 9:
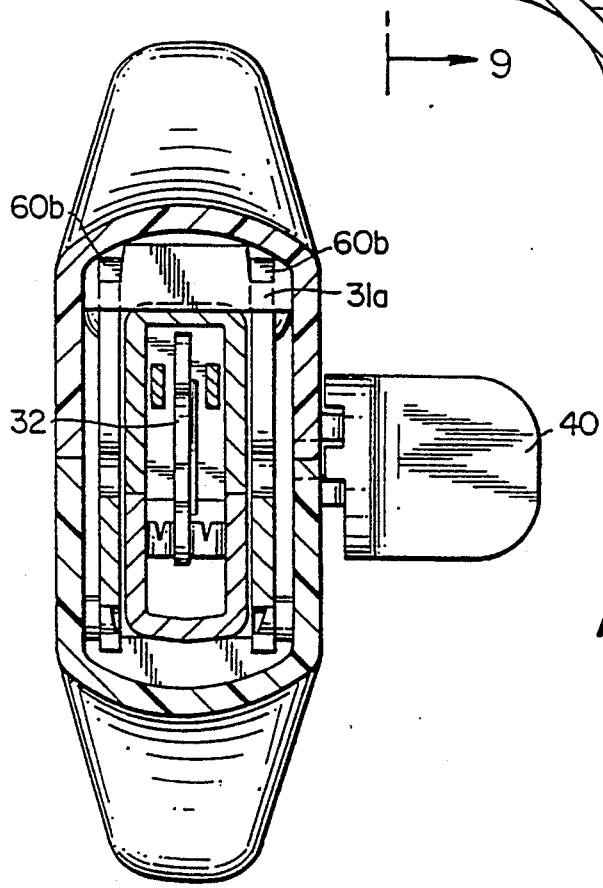
FIG. 9 is a cross-sectional view taken along lines 7—7 of FIG. 8, illustrating the attachment mechanism of FIG. 8.

Referring now to FIG. 8, the mechanism for locking the half sections 12,14 is illustrated in cross-section. Handle clamp 60 (shown in FIG. 4) is pivotally mounted to retainer channel 48 as described previously, and includes distal clamp section 60a having locking fingers 60b. These locking fingers are dimensioned and configured to engage shoulders 31a of anchor 31 attached to fastener cartridge 21 (also see FIG. 3) when the half sections 12,14 are assembled in face to face relation and handle 64 and clamp 60 are pivotally advanced toward half section 14. This movement causes engagement between locking fingers 60b and shoulders 31a of anchor 31 to secure the half sections 12,14 together.

Referring now to FIG. 8, a safety feature of the present apparatus is illustrated. The knife bar 32 includes fastener shoe 44 attached to the distal end portion 32a as shown, and retainer shoe 46 attached to the distal end portion 32b as shown (also, see FIG. 3). When the half sections 12,14 are fully assembled and handle 64 and clamp 60 are closed distal movement of finger pad 40 is made possible, causing corresponding distal movement of cam bars 34,36 and knife bar 32. With this motion, retainer shoe 46 and fastener shoe 44 slide distally within the respective channels defined by fasteners shoe plate 30 and retainer shoe plate 50. It will be readily appreciated that any distal movement of finger pad 40 will cause the shoes 44,46 to enter their respective channels and prevent separation of the half sections 12,14 in the event handle 64 and clamp 60 are inadvertently urged toward the unlocked position. Continued distal motion results in transverse movement of fastener pushers to cause sequential closure of the fasteners with the retainers.

Figure 11:
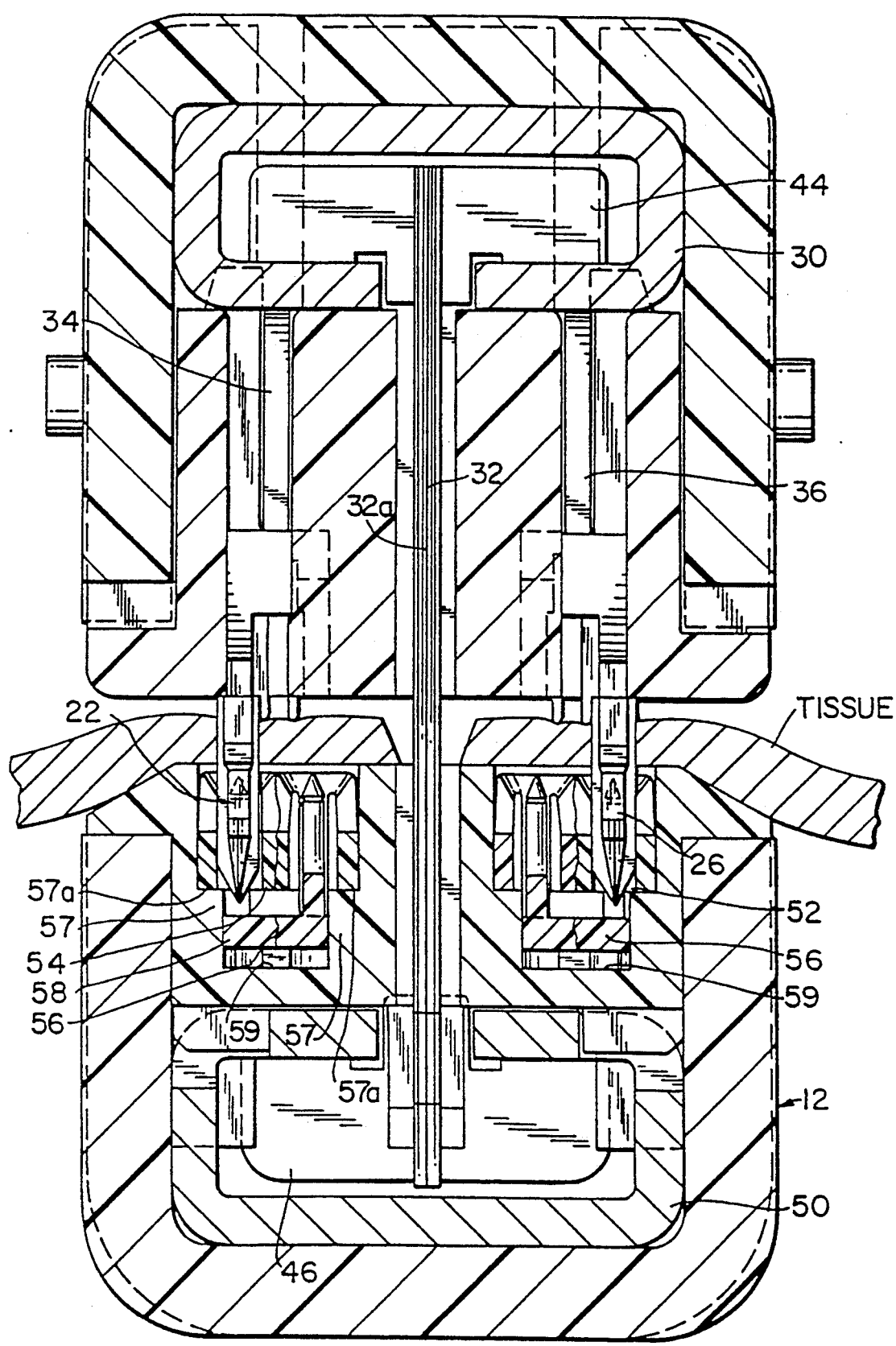
FIG. 11 is a view similar to FIG. 10, illustrating the fasteners and retainers after firing the apparatus.
Figure 12:
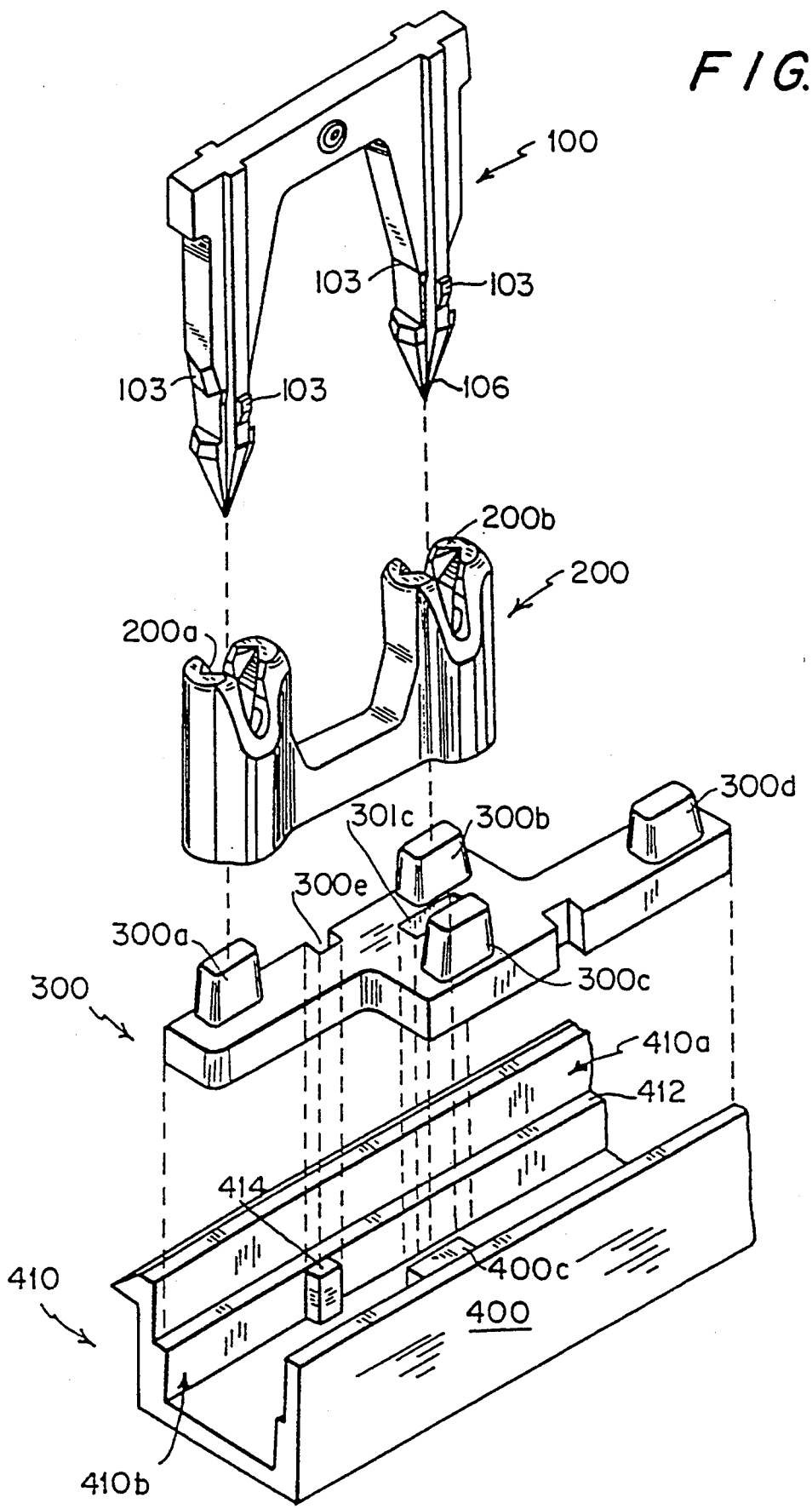
FIG. 12 is a more detailed exploded perspective view of a two-part surgical fastener shown with the retainer mounting element and the retainer holding cartridge of the present invention.
Figure 13A:
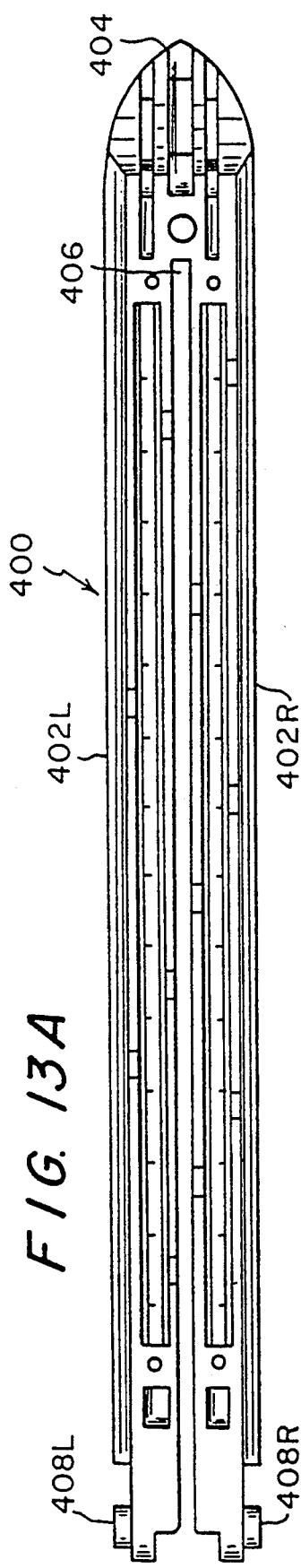
FIGS. 13A, 13B, 13C and 13D are respectively, plan elevational, bottom, and cross-sectional views providing further details of the retainer holding cartridge.
Figure 13B:
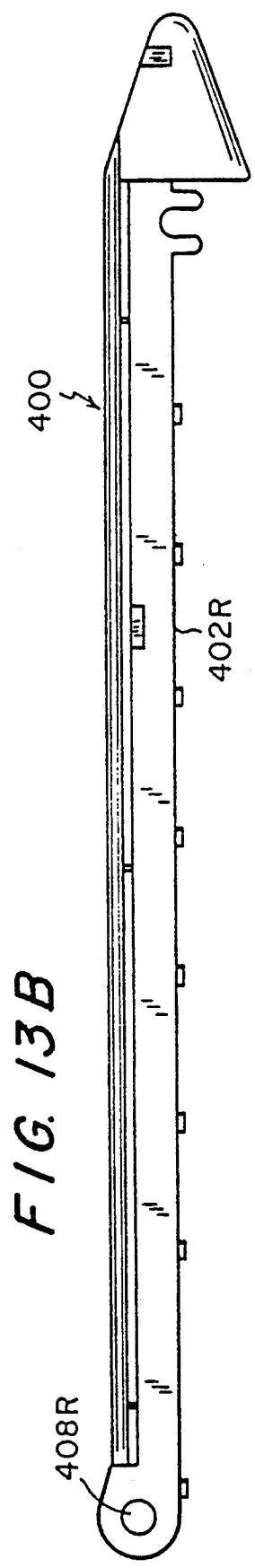
Figure 13C:
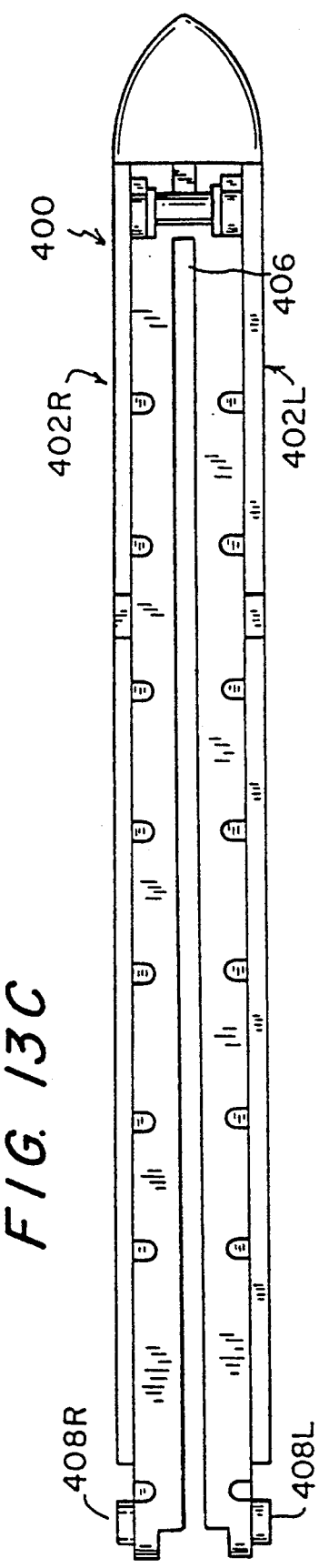
Figure 13D:
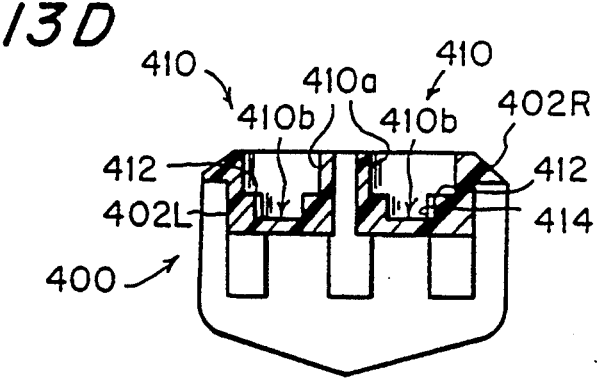

FIG. 10 illustrates the half sections 12,14 in the pre-fired positions and FIG. 11 illustrates the half sections 12,14 of the apparatus after the fasteners are fired and the tissue is cut. Similarly, FIGS. 12, 13 and 14 illustrate the fastener and retainer system in exploded view. Referring now to FIG. 10 in conjunction with FIGS. 1 and 2, a cross section of the fastener system illustrates fastener half section 14 with exemplary fastener 22 and half section 12 with exemplary retainer 54. Retainer holder 58 secures retainer 54 in precisely correct aligned position by insertion of posts 51 into the apertures of the retainer on the side opposite the fastener entry side. FIG. 11 illustrates the half sections shown in FIG. 10 after firing the finger activated finger pad 40 which cause the following simultaneous actions:

1) knife 32a cuts tissue as shown.
2) fastener cam bars 34, 36 sequentially engage fastener pushers 24, 28 causing movement of the fasteners 22, 26 toward retainers 52, 54 such that the fasteners engagably enter the retainer openings and simultaneously push retainer holders 56 deeper into the cartridge 50 while releasing the hold which holders 56 previously had on retainers 52, 54. This position causes the resilient spear shaped leading edge of the absorbable two part fasteners 22,26 to be securely retained within the retainers 52, 54 which are dimensioned and shaped for corresponding locked interference fit with the fasteners. While this fastening action occurs the retainers 52,54 are supported on surfaces 57a of side shelves—or rails—57 as shown in FIG. 11. Thus, the tissue halves become securely fastened by the dual staggered rows of fasteners on each side of the cut and the organs are joined to form a single hollow chamber.

The downward motion of the fasteners is aligned precisely with the retainer openings due to the alignment of the retainers as secured by the holders 54 and the uniform downward motion provided by the fastener pushers 24. The second (or distal) sloped surface 68b of the same pusher, as shown in FIG. 4 facilitates proximal movement of cam bars 34,36.

Referring now to FIGS. 12-17, the inventive fastener and retainer system constructed according to the present invention is shown in exploded perspective views providing additional details of the fastener locking systems. For convenience of illustration in connection with these Figures, the numerals of the components shown in FIGS. 12 et seq. are numbered, beginning with 100. Thus, certain elements in these Figures will bear numerals differing from those utilized in the previous Figures.

Referring to FIG. 12, fastener 100 has a spear shaped tip 106 dimensioned for forced entry into apertures 200a and 200b of retainer 200. Bumps 103 help to retain fastener 100 within retainer 200 after entry has been completed. In FIG. 12 bumps 103 are shown at two locations. Bumps 103 are also provided on the rear face of fastener 100 (not shown) to retain the fastener. Retainer 200 is securely positioned on retainer holder 300 having upstanding posts 300a, 300b, 300c, 300d which are dimensioned and configured to enter apertures 200a and 200b of retainers 200 on the side opposite the fastener entry side. The retainer holder 300 provides a stable flat base for the retainer and disengages from the retainer when the fastener portion engages the retainer. As noted hereinabove, during the operation of the instrument the fasteners are ejected from the fastener holding cartridge to mate with their respective retainers. Further details of novel retainer holding cartridge 400 may be seen by referring to FIGS. 13A, 13B, 13C and 13D.

Retainer holding cartridge 400 is an elongated piece having two members 402L and 402R longitudinally extending proximally from the distal end 404 of the retainer holding cartridge 400. Left and right members 402L and 402R define a center longitudinal slot 406 for receiving the distally moving knife member 32 described hereinabove. In one embodiment, the proximal ends of members 402L and 402R have outwardly projecting pins 408L and 408R respectively, for pivotally mounting to a surgical fastener applying instrument. Alternatively, these pins could be eliminated. Each member 402L and 402R has a compartment 410 comprising a relatively wide upper vertical walled channel 410a for seating one or more retainers, and a relatively narrow vertical walled lower channel 410b for mounting the retainer mounting elements. The difference in widths between the upper and lower channels defines shelves 412 on both sides of the compartment which support the retainers and act as a backstop. The lower channel 410b is adapted to hold retainer holders 300 in a frictional fitting such that they are frictionally supported in an initial upper position wherein the retainer holders 300 are engaged with the retainers 200. The retainer holders 300 are downwardly slidable when forced out of engagement with the retainers 200 by the entering prongs of the fastener portions 100. Vertical guide rails 414 on the sides of the channels cooperate with slots 300e formed in retainer holder 300 to reduce the unwanted torquing of the retainer holders 300 and prevent the retainer holders 300 from moving distally or proximally. In the alternative, vertical post 400c may be provided to engage an aperture 301c in the retainer holder 300. See, also, post 51 engaging aperture 53 as shown in FIG. 5. Alternatively, the retainer cartridge 400 could be provided with both a vertical guide rail 414 on each side to engage a respective side slot 300e in retainer holder 300, and a central post 400C as shown in FIG. 12 dimensioned to be received in aperture 301C in retainer holder 300.

Figure 14A:
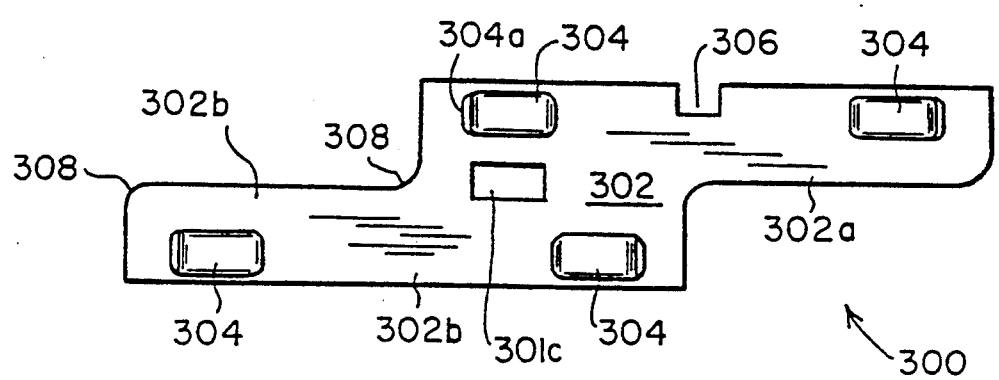
FIGS. 14A and 14B are plan views of left hand, and right hand retainer mounting elements, respectively.
Figure 14B:
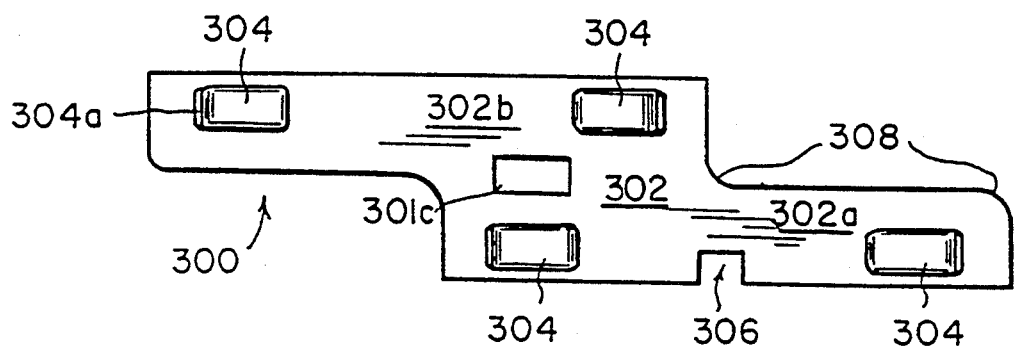
Figure 15:
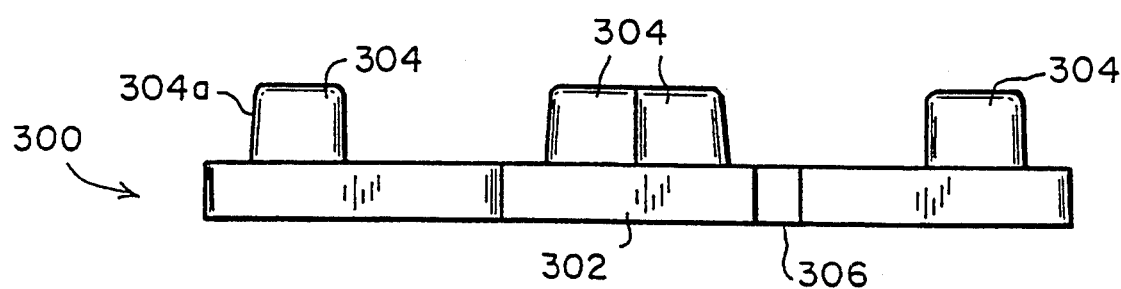
FIG. 15 is a side elevational view of the retainer mounting element of FIG. 14B.

Referring now to FIGS. 14A, 14B and 15, further details of the retainer holders are shown. Retainer holder 300 includes a base 302 having two integrally connected substantially rectangular portions 302a and 302b, and a plurality of upright posts 304 for entry into the apertures on the bottom portion of the retainer as described hereinabove. The base has a vertical notch 306 for slidably engaging guide rails 414 of the retainer cartridge 400. Rounded corners 308 enable a smoother sliding fit between the convex corner of one retainer mounting element being adapted to fit into the concave corner of another mounting element. As noted, the width of base 302 is such that the retainer mounting element 300 is retained in the lower channel 410b by friction, or slight interference fit, although the retainer mounting element 300 is slidable in the vertical direction. The uprights 304 ideally each have a sloped side 304a which is angled slightly off the vertical such that the top of the upright is slightly narrower than the bottom. The tapering facilitates the entry and removal of the uprights from the retainer apertures.

Figure 17:
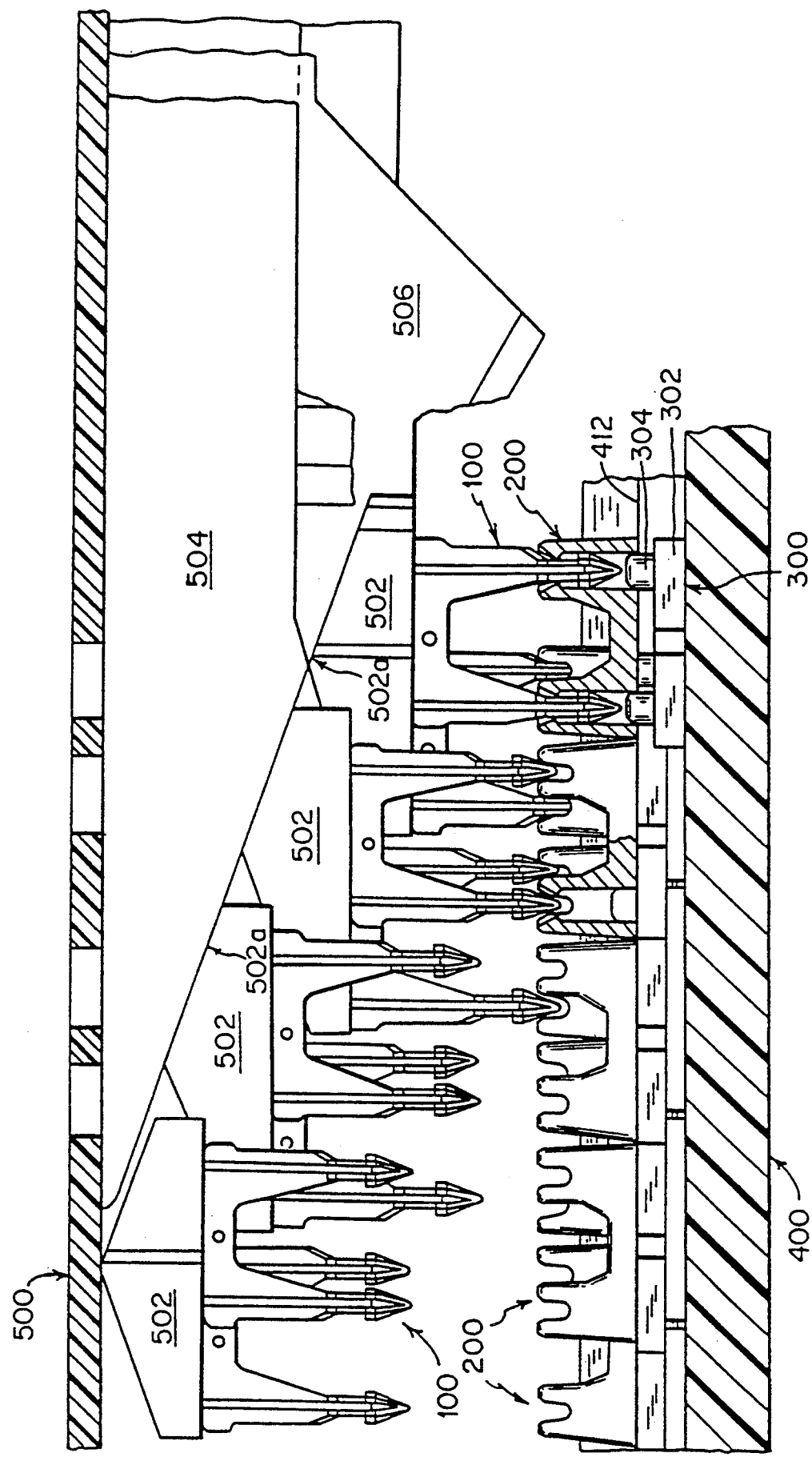
FIG. 17 illustrates in cross-sectional view, the two part surgical fasteners being joined in an apparatus employing the present invention.

Referring now to FIGS. 16A, 16B and 17, the retainers 200 are initially in the position illustrated in FIG. 16A. The retainer 200 is located in the upper chamber 410a, and mounted on retainer holder 300 by means of uprights or posts 304 which are inserted into the apertures 202 at the bottom of the retainer 200. A portion of the bottom of the retainer 200 overlaps the edge of base 302 such that the overlapping portion rests on shelf 412.

Retainer holder 300 is slidably mounted within the lower channel 410b of the cartridge 400 with notch 306 in engagement with guide rail 414.

When the fasteners 100 are inserted into retainers 200, the barbed tips 106 of the fasteners push down on the uprights 304, thereby pushing the retainer mounting element 300 down into a position where it is no longer in engagement with the retainer 200. The retainers 200 are supported by shelves 412 such that they are braced against downward movement. Upon disengagement with the retainer holders 300, the retainers 200 are free to be lifted out of the cartridge 400 in engagement with the fasteners.

FIG. 17 illustrates in further detail, the operative portion of the apparatus for applying surgical fasteners, employing the fastener and cartridge system of the present invention as described hereinabove. The fastener holding cartridge 500 contains fastener pushers 502, cam bar 504, and optionally a knife 506. When actuated, the cam bar 504 is moved distally, thereby contacting the sloped camming surface 502a of pusher elements 502 and urging the fastener portions downward into the retainer cartridge 400 where fastener 100 engages its respective retainer 200. As described above, the cam bar 504 operates upon the pusher elements 502 sequentially, first contacting the proximal end of each pusher element. As noted, because of this movement there may be a tendency for unwanted torque to develop which might otherwise cause a relative clockwise pivoting of the fastener. Flat mounting element bases 302 and shelves 412 help insure that the retainers 200 do not pivot appreciably.

In use, the apparatus is positioned such that a layer of body tissue is situated between the fastener holding cartridge 500 and the retainer holding cartridge 400. When the apparatus is actuated the fastener barbs 106 will penetrate the tissue layer and lock into the retainer 200, thereby sealing the tissue. Although FIG. 17 shows the fasteners 100 moving downwardly, the direction of movement to engage retainer 200 will obviously depend upon the orientation of the apparatus during use.

The apparatus as described hereinabove is preferably constructed as a disposable apparatus suitable for a single use. However, the apparatus is readily adaptable to a multiple use or non-disposable form merely by structuring the fastener and retainer cartridges so as to be replaceable within their respective channels. In such case, replacement of the knife bar 32 with knife blade 35 is also desirable in order to assume precise and accurate cutting of the tissue. The cam bars 34,36 could also be replaceable along with knife 32. In the preferred form, the components are constructed of steel except for the cartridges, and the finger pad 40 which are constructed of a suitable plastic material such as nylon or polycarbonate. The preferred fastener and retainer are composed of a bioabsorbable polymeric material, such as polymers or copolymers of glycolide, lactide, p-dioxanone, polyester, polyamino acids and the like, the preferred construction of which is shown and described in U.S. Pat. No. 4,932,960, which is hereby incorporated by reference.

What is claimed is:

1. Apparatus for applying at least two rows of two-part surgical fasteners, each surgical fastener having a fastener portion and a retainer portion, which comprises:
    a) a first section having a plurality of said fastener portions of said two-part fasteners supported thereby, said fastener portions arranged in at least two rows;
    b) a second section engageable with said first section and having a plurality of said retainer portions of said two-part fasteners supported thereby, said retainer portions arranged in at least two rows and supported in positions opposite said fastener portions, said first and second sections being relatively movable to clamp body tissue therebetween; and
    c) at least two cam bars movable within the first section and an actuating member for moving the at least two cam bars longitudinally for sequentially driving said fastener portions toward said retainer portions in a direction generally transverse to the direction of movement of said at least two cam bars and into engagement with each other.

2. Apparatus according to claim 1 wherein a first row of said at least two rows is disposed on one side of a generally central longitudinal axis and arranged in general longitudinal alignment therewith, and a second row of said at least two rows of fastener portions is disposed on the other side of the longitudinal axis and arranged in general longitudinal alignment therewith.

3. Apparatus according to claim 2 wherein a first row of said at least two rows of retainer portions is disposed on one side of the longitudinal axis and positioned opposite said first row of said fastener portions, a second row of said at least two rows of retainer portions is disposed on the other side of the longitudinal axis and positioned opposite said second row of said fastener portions.

4. Apparatus according to claim 3 wherein one of said at least two cam bars is disposed on one side of the longitudinal axis and positioned to sequentially drive said first row of fastener portions, and a second of said at least two cam bars disposed on the other side of the longitudinal axis and positioned to sequentially drive said second row of fastener portions.

5. Apparatus according to claim 1 further comprising a knife disposed between said at least two cam bars for cutting the body tissue.

6. Apparatus according to claim 5 wherein said first section comprises at least two rows of apertures dimensioned and configured for frictionally detachably holding said at least two rows of said fastener portions.

7. Apparatus according to claim 6 wherein said second section comprises at least two rows of retainer portion holders having means for supporting said retainer portions in position for reception of said fastener portions.

8. Apparatus according to claim 7 wherein each said retainer portion holder comprises at least two upstanding posts extending generally transversely relative to a plane defined by said retainer portion holder, said at least two upstanding posts dimensioned and configured to be received within correspondingly dimensioned and configured apertures formed in said retainer portions to support said retainer portions within said second section.

9. Apparatus according to claim 8 wherein each said retainer portion holder comprises two pairs of said upstanding posts, a first pair of said upstanding posts positioned and dimensioned to enter into first and second apertures of a first retainer portion, a second pair of said upstanding posts positioned and dimensioned to enter into first and second holes of a second retainer portion.

10. Apparatus according to claim 5 wherein said knife comprises a knife bar extending in a generally longitudinal direction.

11. Apparatus according to claim 10 wherein said at least one cam bar and said knife bar are each operatively connected to a manually operable finger pad adapted for slidable longitudinal movement, whereby distal longitudinal movement of said finger pad causes corresponding distal movement of said at least one cam bar to sequentially advance said fastener portions into engagement with their respective retainer portions and causes distal movement of said knife bar to cut the body tissue adjacent the location of the application of said fasteners.

12. Apparatus according to claim 11 wherein said knife bar comprises a knife edge at a distal end thereof.

13. Apparatus according to claim 11 wherein said knife bar lags said at least one cam bar when said at least one cam bar is distally advanced.

14. Apparatus for applying at least two rows of two-part surgical fasteners to body tissue, each surgical fastener having a fastener portion for piercing body tissue, and an apertured retainer portion for receiving said fastener portion, which comprises:
- a frame defining a longitudinal axis;
- a cartridge disposed within said frame for holding a plurality of said fastener portions in generally aligned relation;
- a support member disposed within said frame and positioned opposite said cartridge for holding a plurality of said retainers in positions opposite the respective fastener portion;
- means movable within said cartridge for sequentially driving at least one of said fastener portions and retainer portions into engagement with the other, said driving means adapted to drive said fastener portions in a direction generally transverse to said longitudinal axis of said frame; and
- an actuating member slidably mounted to said frame and adapted for reciprocal longitudinal movement relative to said frame, whereby distal longitudinal movement of said actuating member activates said fastener portion driving means for driving said fastener portions into engagement with said retainer portions.

15. Apparatus according to claim 14 further comprising knife means for cutting body tissue adjacent the location of the applied fasteners.

16. Apparatus according to claim 14, wherein said cartridge is removably disposed on said frame.

* * * * *